United States Patent [19]

Kidd et al.

[11] Patent Number: 4,987,585
[45] Date of Patent: Jan. 22, 1991

[54] X-RAY POSITIONER FOR MULTI-AXIS PROFILING

[75] Inventors: Harold J. Kidd, Waukesha; Paul R. Anderson, Milwaukee, both of Wis.

[73] Assignee: General Electric Company, Milwaukee, Wis.

[21] Appl. No.: 560,500

[22] Filed: Jul. 25, 1990

Related U.S. Application Data

[63] Continuation of Ser. No. 333,291, Apr. 4, 1989, abandoned.

[51] Int. Cl.$^5$ .............................................. H05G 1/02
[52] U.S. Cl. .................................... 378/197; 378/193
[58] Field of Search ............................ 378/195–198, 378/193

[56] References Cited

U.S. PATENT DOCUMENTS

| | | | |
|---|---|---|---|
| 2,818,510 | 12/1957 | Verse | 378/197 |
| 3,617,749 | 11/1971 | Massiot | 378/197 |
| 3,670,163 | 6/1972 | Lajus | 378/196 |
| 3,868,506 | 2/1975 | Ogiso | 378/197 |
| 3,892,967 | 7/1975 | Grady et al. | 378/197 |
| 4,024,403 | 5/1977 | Bernstein et al. | 378/197 |
| 4,150,297 | 4/1979 | Borggren | 378/197 |
| 4,209,706 | 6/1980 | Nunan | 378/197 |
| 4,298,801 | 11/1981 | Heitman et al. | 378/196 |
| 4,358,856 | 11/1982 | Stivender et al. | 378/167 |
| 4,363,128 | 12/1982 | Grady et al. | 378/181 |
| 4,365,343 | 12/1982 | Grady et al. | 378/181 |
| 4,412,346 | 10/1983 | Takenouti et al. | 378/181 |
| 4,501,011 | 2/1985 | Hauck et al. | 378/196 |
| 4,541,293 | 9/1985 | Caugant et al. | 74/89.18 |
| 4,653,083 | 3/1987 | Rossi | 378/195 |
| 4,679,223 | 7/1987 | Ohlson et al. | 378/197 |
| 4,716,581 | 12/1987 | Barud | 378/198 |
| 4,756,016 | 7/1988 | Grady et al. | 378/195 |

FOREIGN PATENT DOCUMENTS

| | | | |
|---|---|---|---|
| 3542333 | 6/1987 | Fed. Rep. of Germany | 378/196 |
| 0155937 | 12/1981 | Japan | 378/197 |

*Primary Examiner*—Craig E. Church
*Attorney, Agent, or Firm*—Quarles & Brady

[57] ABSTRACT

A multi-axis profiling x-ray machine for making angiographic examinations includes an L arm rotatable about a first machine axis intersecting an isocenter, the L arm defining a second machine axis intersecting the isocenter and perpendicular to the first machine axis. An offset arm is rotatable about the second machine axis, and includes a curved guide collar holding C arm. The C arm slides along the collar to move an x-ray source mounted on one end of the C arm and an image receiver mounted on the other end of the C arm about a third machine axis perpendicular to the second machine axis. The three axes permit isocenter profiling motion about an arbitrary angle in three dimensions.

5 Claims, 4 Drawing Sheets

X-RAY POSITIONER FOR MULTI-AXIS PROFILING

This is a continuation of application Ser. No. 07/333,291, filed Apr. 4, 1989, now abandoned.

BACKGROUND OF THE INVENTION

This invention relates to medical diagnostic x-ray apparatus and in particular to an x-ray apparatus for angiographic procedures.

X-ray equipment generally adapted to the needs of angiography is disclosed in U.S. Pat. No 4,358,856 issued on Nov.9, 1982 to P. Stivender et al. and shown schematically in FIG. 1(a). This equipment is comprised generally of opposing x-ray source 16 and an image receiver 14 mounted at either end of a "U" arm 12 and directed along an image axis 96 through an isocenter 80. An "L" arm 10 is pivoted on a first pivot 20 about a first machine axis 76, and supports a second pivot 18 on a second machine axis 78 perpendicular to the first machine axis 76. Rotation about the first and second machine axes permits imaging along an arbitrary image axis 96. Table 92, shown in phantom, is included to provide reference as to the position of a patient (not shown)

As shown in FIG. 1(b), a second approach used in the construction of angiographic x-ray equipment, and disclosed in U.S. Pat. No. 4,150,297 issued on Apr. 17, 1979 to Borggren comprises a "C" arm 22 in lieu of a U arm 12. In this approach the L arm 10 is pivotably mounted on a support beam 28 rather than on the floor to rotate about a first axis 76. The C arm 22 does not pivot about a second pivot on the L arm 10 but rather slides through a supporting collar 24 so as to cause the x-ray tube 16 and image receiver 14 located at either end of the C arm 22 to rotate about a second machine axis 78 perpendicular to the plane of the C arm 22. The radius of the C arm 22 is such as to position this second machine axis to intersect the isocenter 80. Therefore the resulting combined motion of the L arm and the C arm result in isocentric motion of the image receiver 14 and the x-ray source 16. The geometric analysis of a C arm system of FIG. 1(b) is similar to that of the U arm system of FIG. 1(b) after allowing for the 90° offset of the first and second machine axis 76 and 78.

The above described L arm and C arm systems are not well adapted to certain radiographic procedures used to locate obstructions within the channel or lumen of a blood vessel. Referring to FIG. 2(a), plaque 42, such as that associated with arteriosclerotic disease, constricts the lumen 44 of coronary vessel 40. If the constriction is not concentric in cross section, as shown in FIG. 2(a), the constriction may not be apparent in a first projection of the vessel orientated perpendicularly to the vessel's major axis 50. Such a projection is shown in FIG. 2(c) as taken along projection angle 48 depicted in FIG. 2(a). At a different projection angle, however, such as angle 46 shown in FIG. 2(a), the constriction may be clearly visualized as shown in the projection of FIG. 2(b). Generally, in order to accurately assess the extent of the constriction of a vessel, the vessel must be "profiled" from several different angles. This requires that the image axis of the x-ray machine be rotated about the major axis of the vessel within a "profiling" plane perpendicular to the major axis of the vessel. In the case of the coronary arteries, this profiling plane may have a nearly arbitrary orientation corresponding to the many possible artery major axes. Each profiling plane may be identified by a "profiling plane axis" which is identical to the major axis of the vessel being profiled and perpendicular to the profiling plane.

Motion within an arbitrary profiling plane is difficult to achieve with the L arm and C arm systems described above. With such systems, profiling with a profiling plane axis which is not perpendicular to the first machine axis of the x-ray machine requires the simultaneous motion of both the L and U arm or L and C arm axes. Important, for profiling plane axes nearly parallel to the first machine axis, the L arm must swing through approximately the same arc as the arc that the image axis moves within the profiling plane. Such large L arm motion may be undesirable during a medical procedure to the extent that it interferes with equipment positioned near the operating table and disrupts the medical professionals attending the procedure.

A constant profiling motion, in the above described L and C systems, also requires that the relative speed and direction of the L and U arm or L and C arm axes be continually adjusted according to complex trigonometric relationships which are dependant on the relative location of each axis and the profiling plane axis. In most situations accurate profiling control of these systems is not possible under the direct control of a human operator.

SUMMARY OF THE INVENTION

In accordance with the invention, a diagnostic x-ray machine for multi-axis profiling of a human body includes a first arm rotatable on a first machine axis, said first arm supporting a second arm rotatable about a second machine axis perpendicular to the first machine axis.

The second arm supports a third arm rotatable about a third machine axis perpendicular to the second machine axis. Attached to a first end of the third arm is an image receiver and attached to a second end is an x-ray source. The x-ray source and the image receiver are directed radially inward along an imaging axis. Motion of the third arm rotates the image axis around the third machine axis and within a plane perpendicular to the third machine axis.

Profiling of a anatomical vessel is accomplished by performing the steps of positioning the first and second arm so as to align the third machine axis along the major axis of the vessel to be profiled. A first profiling image is then obtained along a first profiling angle. The third arm is then positioned to a second profiling angle and a second profiling image is obtained.

It is one object of the invention to permit profiling motion with movement of only a single machine axis. The first and second machine axes, associated with the L arm and offset arm respectively, permit alignment of the third machine axis, associated with the C-arm, along the major axes of the vessel being profiled. Profiling motion may then be obtained with motion of only the C arm.

It is yet another object of the invention to minimize interference with equipment and personnel from axis movement during a radiographic procedure. The geometry of the present invention permits profiling and most changes in angular position of the image axis to be accomplished, after initial positioning, without motion of the L arm. Motion of the L-arm, which is pivoted to the floor, may be more disruptive than motion of the other axes.

It is another object of the invention to realize the above described profiling capability with a structure that minimizes C arm radius while maximizing the distance from the isocenter to any portion of the machine support structure as measured along the second machine axis (throat depth). The use of the offset arm in conjunction with offset mounting of the x-ray source and the image receiver, increases the throat depth by removing the bulk of the C arm collar from the path of the second machine axis. Alternatively, this displacement permits the C-arm radius to be decreased while maintaining a constant throat depth.

It is yet another object of the invention to realize the above described multi-axis profiling capability without significantly decreasing the access angle to the patient. The use of a C arm for the final axis improves the angle of access over that which would be obtained by the use of a U arm in a three axis configuration. Measurement of the access angle will be discussed further below.

The foregoing and other objects and advantages of the invention will appear from the following description. In the description, reference is made to the accompanying drawings which form a part hereof and in which there is shown by way of illustration, a preferred embodiment of the invention. Such embodiment does not necessarily represent the full scope of the invention, however, and reference is made therefore to the claims herein for interpreting the scope of the invention.

BRIEF DESCRIPTION OF THE DRAWINGS

FIGS. 1 and 2 have been discussed in the Background of the Invention section;

DESCRIPTION OF THE PREFERRED EMBODIMENT

Figure 3:
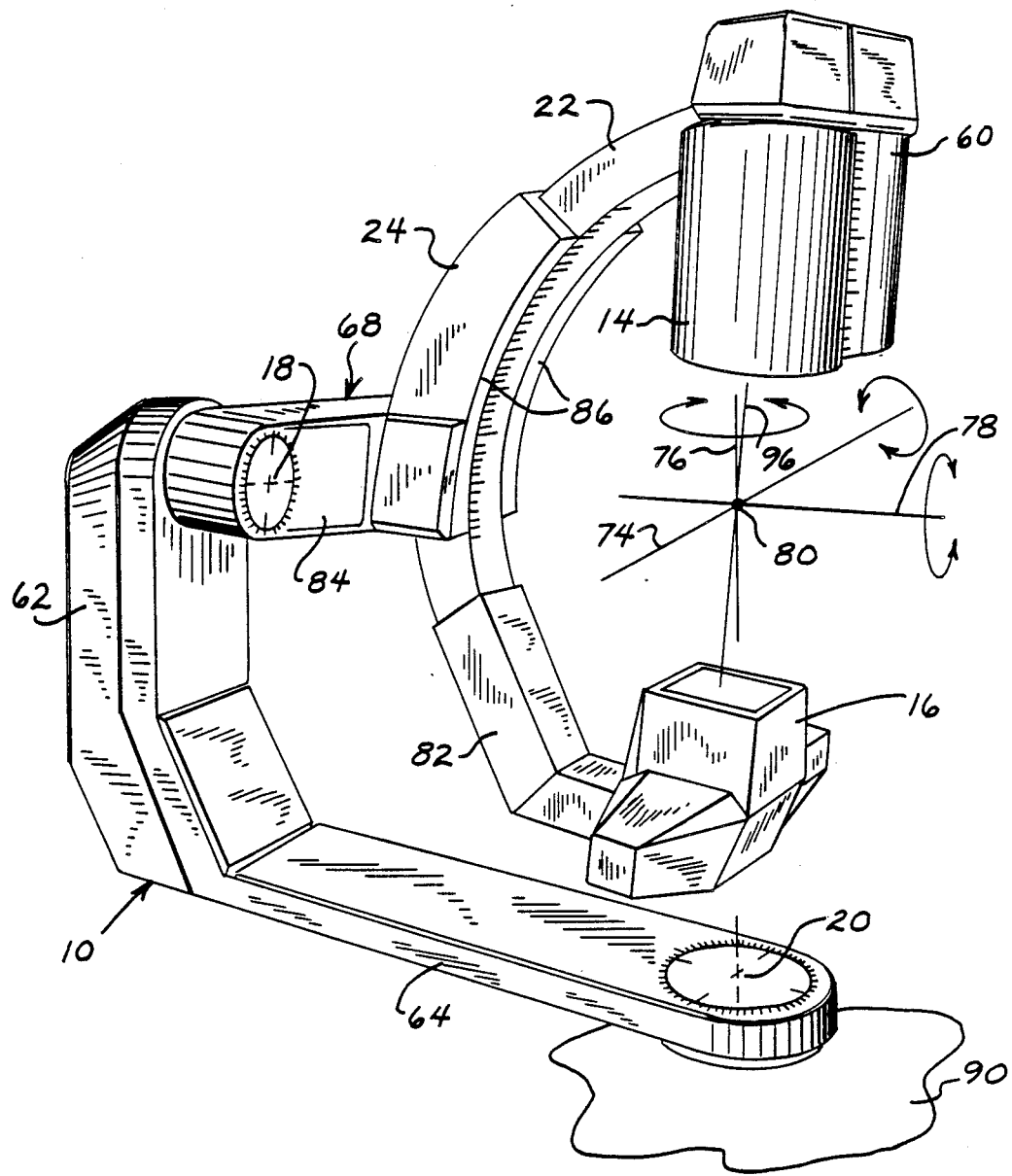
FIG. 3 is a perspective view of an x-ray machine constructed according to the present invention.

Referring to FIG. 3, a multi-axis profiling x-ray machine is supported by an L-arm 10 comprised of L arm base 64 and L arm riser 62. The L arm base 64 is affixed to the floor 90 though a first pivot 20. The first pivot 20 permits the L arm base 64 to swing through an arc of 190° in plane parallel to the floor 90, about a first machine axis 76 perpendicular to the plane of the floor 90, and concentric with pivot 20. The L arm 10 incorporates an electric motor (not shown) which may drive the L arm throughout its range of travel at a controllable speed from 0°-10° per second. The motor is connected to the L arm 10 by means of slip clutch which permits the L arm 10 to be positioned manually as is understood in the art.

Extending upward and affixed at a right angle to the L-arm base 64 is the L arm riser 62 which supports a pivot 18. Offset arm 68, comprised of offset strut 84 and arcuately curved collar 24 is attached to pivot 18 so as to rotate in an arc concentric with the second pivot 18, within a plane perpendicular to the plane of the floor 90, about a second machine axis 78 which is parallel to the floor 90. The offset strut 84 extends away from the second machine axis 78 at a right angles and is attached to the collar 24.

When the offset strut 84 is positioned to be parallel to the plane of the floor, it may be rotated in an arc of 115° in clockwise or counterclockwise direction about the second machine axis 78. The rotation of the offset arm 68 is accomplished by means of an electric motor and gear box (not shown) incorporated into the L-arm riser 62 as is understood in the art. The offset arm 68 may be driven by the electric motor at a variable speed of up to 10° per second. The first and second axes 76 and 78 intersect at isocentric point 80, which is approximately 42 inches above the floor 90.

The collar 24, attached to the free end of offset strut 84, slidably receives arcuately curved C arm 22 in a manner such that the curve of C arm 22 faces away from the L arm riser 62 but is within the C arm plane parallel to, but offset from, the second machine axis 78. The C arm plane is offset 13.5 inches from the second machine axis 78 by the offset strut 84. This offset increases the x-ray machine's throat depth as will be described below.

The collar 24 is comprised of two arcuately curved guides 86 conforming to the radius of the C arm 22 which retain and support the C arm 22 and allow it to slide, within the guides 86, about a third machine axis 74 perpendicular to the second machine axis 78 and intersecting the first and second axes at the isocentric point 80. The C arm 22 is supported by a track and bearings (not shown) engaged by the collar guides 86 and may be moved within the collar guides 86 by means of an electric motor (also not shown) incorporated into the collar 24. The electric motor may drive the C arm 22 about the third machine axis 74 at an angular speed of up to 10° per second.

A first end of C arm 22 is affixed to slide support 60 which in turn holds the image receiver 14. The image receiver 14 may be an image intensifier that converts a x-ray image to a visible light image for capture by television camera or a film cassette as is generally understood in the art.

X-ray source 16 is attached to the second end of the C arm 22 by means of tangent arm 82, and spaced at 180° from the image intensifier 14 along the curve defined by the C arm. The x-ray source 16 and image receiver 14 face each other along an image axis 96. The x-ray source 16 is orientated so that the center line of the x-ray beam is directed along the image axis 96 and the image receiver 14 is orientated to receive the x-ray beam. The image receiver 14 may be moved along the image axis 96 by movement of the slide support 60 toward or away from the x-ray source 16. This permits the distance between the x-ray source 16 and the image receiver 14 to be varied from approximately 31.5 inches to 45 inches to control the x-ray image magnification as is understood in the art. The image receiver 14 and the x-ray source 16 are offset from the C arm plane toward the second pivot 18 by an amount equal to the length of the offset strut 84. The effect of this offset mounting is to cause the image axis 96 to intersect the isocentric point 80.

When the image axis 96 is perpendicular to the second machine axis 78, the C arm may slide within the collar about the third machine axis 74 through a range of 45° in either direction.

Figure 1A:
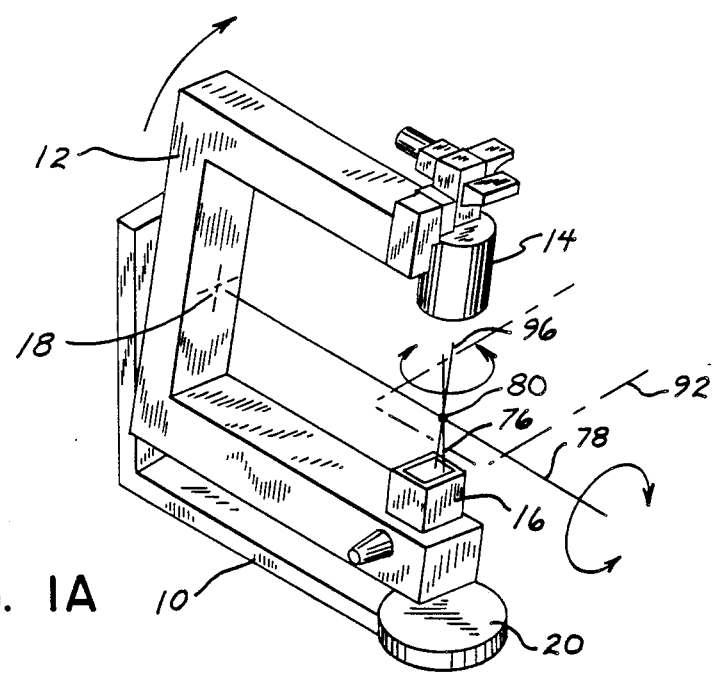
FIG. 1(a) and 1(b) are schematic perspective views of two prior art angiographic x-ray machines.
Figure 1B:
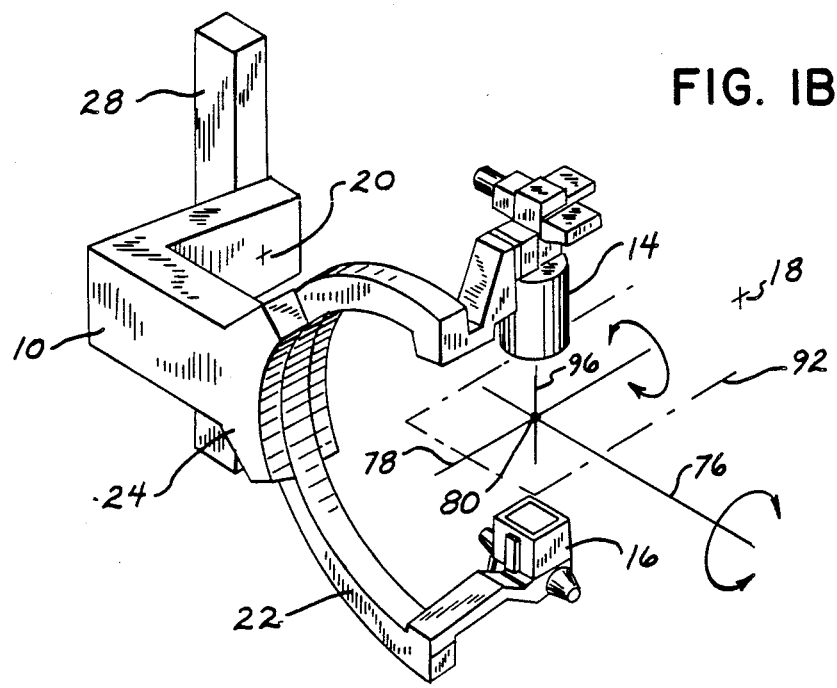
Figure 2A:
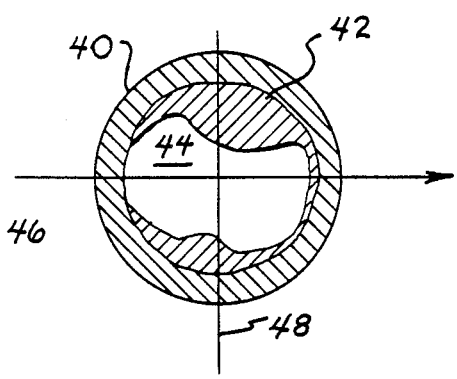
FIG. 2(a) is diagrammatic cross section of a coronary blood vessel showing partial obstruction.
Figure 2B:
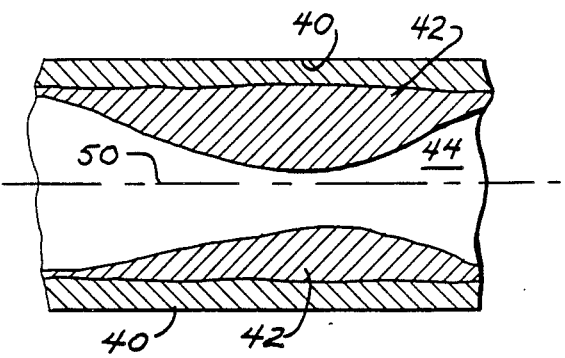
FIGS. 2(b) and (c) are diagrammatic representations of x-ray images of the coronary blood vessel obtained along the axes 46 and 48 as shown in FIG. 2(a).
Figure 2C:
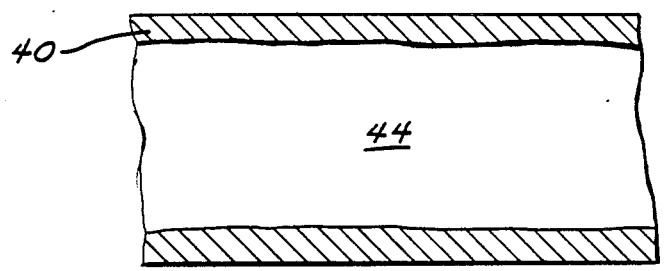
Figure 6A:
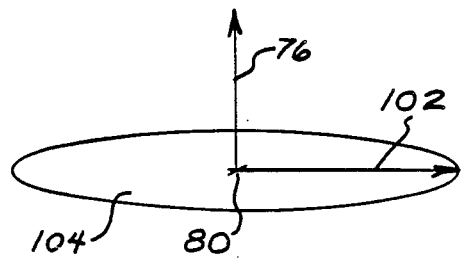
FIG. 6(a) is a diagrammatic geometric representation of the profiling plane axes achievable with a L or C arm machines of FIG. 1.

An important feature of the present invention is its ability to profile, with the movement of a single machine axis, blood vessels whose major axes are not perpendicular to the first machine axis 76. Referring to FIG. 6(a), plane 104, normal to axis 76 and including isocenter point 80, together with axis 76, represent the set of all possible projection plane axes for single machine axis motion for the previously described L and C arm systems of FIG. 1. For example, a profiling plane axis 102 originating at isocenter 80 and lying within plane 104 may be obtained by the L and C arm systems by appropriately positioning L arm 10 and then holding the L arm 10 stationary and rotating the U arm 12 or C arm 22. Profiling along axis 76 is possible by positioning the U or C arm to such that the image axis 96 is perpendicular to the first machine axis 76 then rotating the L arm 10 about the first machine axis. The set of all such profiling plane axes will lie within plane 104 or along axis 76.

Figure 6B:
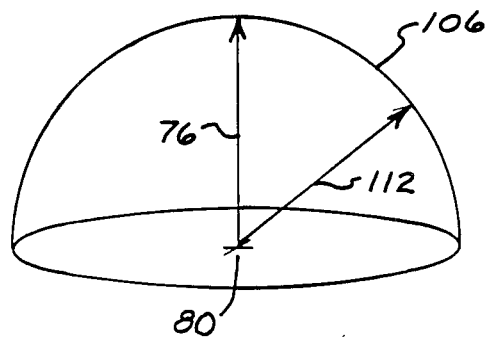
FIG. 6(b) is a diagrammatic geometric representation of the profiling plane axes achievable with the x-ray machine of FIG. 3.

Referring to FIG. 6(b), the present invention may profile vessels whose major axes lie within volume 106. For example profiling plane axis 112 may be obtained by moving the L axis 10 and the offset arm 68 and then holding both the L axis 10 and the offset arm 68 stationary and rotating the C arm 22. The set of all such profiling plane axes will lie in volume 106. In summary, with the present invention, profiling with single axis motion is not limited to profile planes whose axes are perpendicular to the first machine axis 76.

Figure 4:
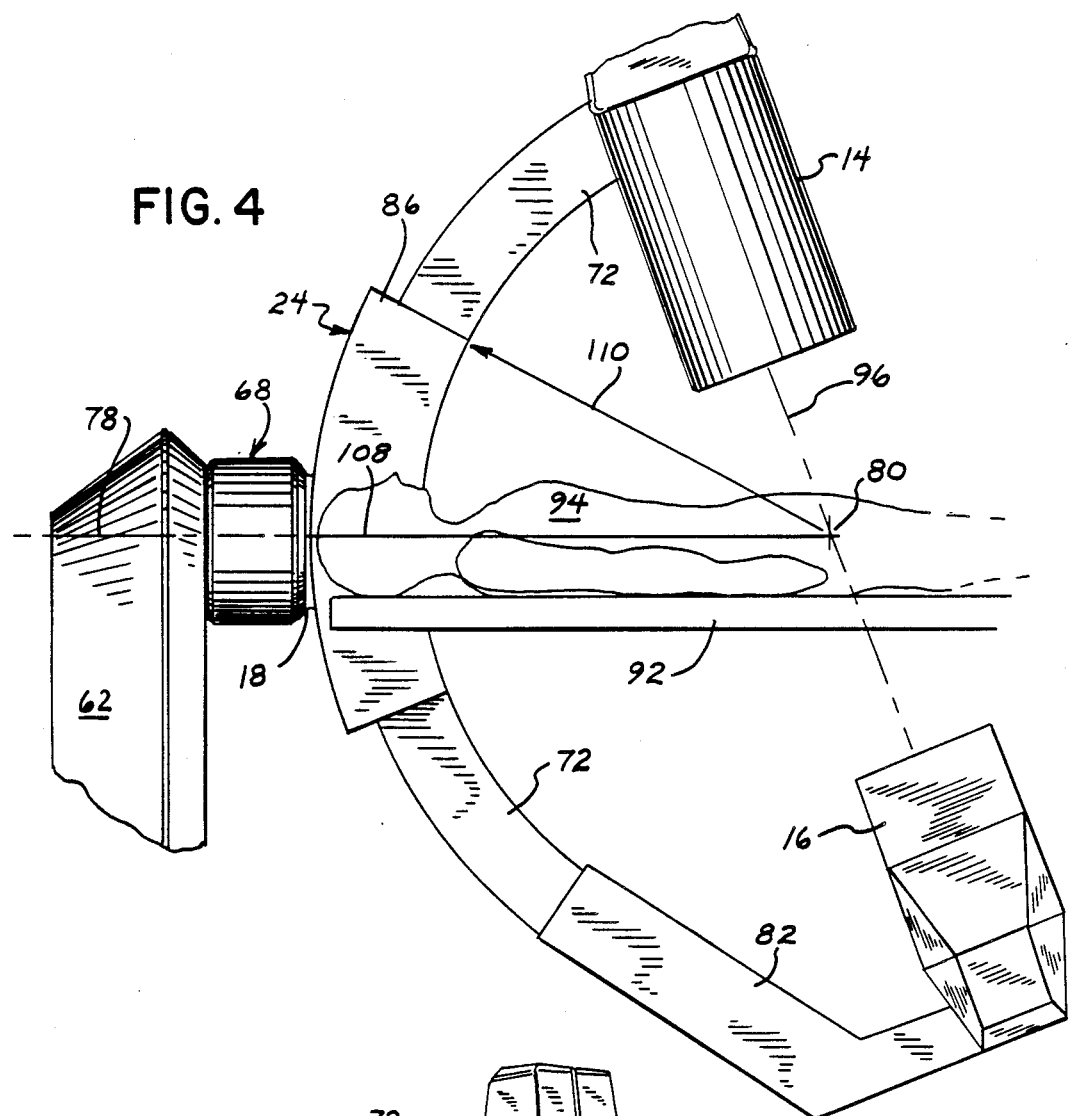
FIG. 4 is a elevation of the x-ray machine of FIG. 3 showing the C arm radius and the throat depth of the x-ray machine. A patient is shown positioned on an exam table.

Another significant feature of this invention is the improved machine throat depth for a given C arm radius. Referring to FIG. 4, a patient 94 is shown positioned on table 92 with respect to the x-ray machine of the present invention. The table 92 is radio-translucent and cantilevered on a support structure (not shown) so as not to interfere with the x-ray imaging process. The offset arm 68 displaces the collar 24 from the second machine axis permitting the patient 94 to be moved closer to the second pivot point 18 than the C-arm radius would otherwise allow. Specifically, with the patient orientated along the second machine axis 78 with head toward the second pivot 18, the isocenter 80 may be positioned at the mid-thigh of the patient for 95% of the male population. This requires an effective throat depth 108 of 42.5 inches whereas the radius of the C arm 110 is only 36 inches. Large throat depth is important in a three axis machine where the patient's orientation with respect to the L arm may be adjusted during a procedure by motion of the L arm. In the two-axis C arm system, previously described, the patient may be oriented so that throat depth is not important.

Figure 5:
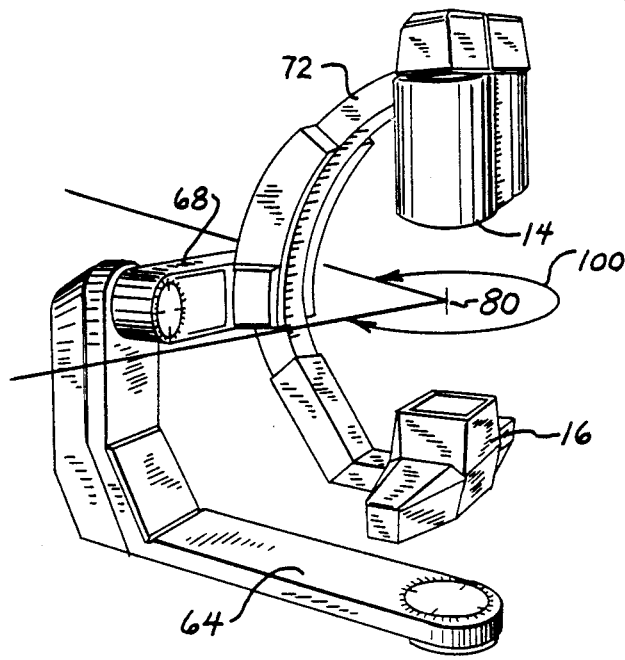
FIG. 5 is a simplified the perspective view of the x-ray machine of FIG. 3 showing the access angle around the isocenter.

Another feature of the present invention is the large access angle provided to the medical personnel using the x-ray machine. Referring to FIG. 5, the access angle 100 measured in a plane around the isocenter 80 perpendicular to the first machine axis, is shown. The access angle 100 indicates those angles from which the isocenter 80 may be approached without interference from the x-ray machine support structure. The use of a C arm 22 to provide the third machine axis 74 of motion ensures an access angle of over 270°. The use of a U arm configuration to provide the third machine axis of motion would be expected to provide less than 270° of access angle in some cases as a result of the larger offset arm 68 that would be required.

A preferred embodiment of the invention has been described, but it should be apparent to those skilled in the art that many variations can be made without departing from the spirit of the invention. For example, the first pivot need not be attached to the floor but could be attached to the ceiling or wall to provide additional clearance to medical personnel. Additionally, the x-ray source could be mounted on a slide to permit adjustment of the x-ray source to isocenter distance.

I claim:

1. A diagnostic x-ray machine for making examinations of a human body comprising:
   an L arm means for rotating on a first pivot about a first machine axis intersecting an isocenter, said L arm including a second pivot defining a second machine axis intersecting the isocenter and perpendicular to the first machine axis;
   an offset arm means for rotating on the second pivot about the second machine axis, the offset arm including an arcuately curved guide collar;
   a C arm means arcuately curved and carried by the curved guide collar for movement therealong, said C arm having first and second opposing ends, said ends revolving about a third machine axis during movement of the C arm relative to the curved guide collar, said third machine axis intersecting the isocenter;
   an x-ray source mounted on the first end of the C arm for directing radiation inward with respect to the third machine axis, along an image axis intersecting the isocenter; and
   an image receiver means mounted on the second end of the C arm for receiving radiation from the x-ray source directed along the image axis.

2. The diagnostic x-ray machine of claim 1 wherein the first machine axis is substantially vertical.

3. The diagnostic x-ray machine of claim 2 wherein the offset arm is comprised of an offset strut extending perpendicularly to the second machine axis from the second pivot and wherein the arcuately curved guide collar is affixed to a free end of the offset strut.

4. The diagnostic x-ray machine of claim 2 wherein the image receiver means includes a support slide means for providing radial motion of the image receiver means with respect to the third machine axis.

5. The diagnostic x-ray machine of claim 2 wherein the first and second opposing end of the C arm are spaced at substantially 180° along the arc defined by the C arm.

* * * * *